(12) United States Patent
Jonas et al.

(10) Patent No.: US 10,729,918 B2
(45) Date of Patent: Aug. 4, 2020

(54) CRYOSTAT AND SYSTEM FOR COMBINED MAGNETIC RESONANCE IMAGING AND RADIATION THERAPY

(71) Applicant: KONINKLIJKE PHILIPS N.V., Eindhoven (NL)

(72) Inventors: Philip Alexander Jonas, Delmar, NY (US); Johannes Adrianus Overweg, Hamburg (DE); Viktor Mokhnatyuk, Castleton On Hudson, NY (US); Avery Montembeault, Niskayuna, NY (US); Martin King, Latham, NY (US); Alan Finder, Latham, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1257 days.

(21) Appl. No.: 14/898,769

(22) PCT Filed: Jun. 5, 2014

(86) PCT No.: PCT/IB2014/061962
§ 371 (c)(1),
(2) Date: Dec. 16, 2015

(87) PCT Pub. No.: WO2014/203105
PCT Pub. Date: Dec. 24, 2014

(65) Prior Publication Data
US 2016/0136456 A1 May 19, 2016

Related U.S. Application Data

(60) Provisional application No. 61/882,924, filed on Sep. 26, 2013, provisional application No. 61/837,739, filed on Jun. 21, 2013.

(51) Int. Cl.
*H01F 1/00* (2006.01)
*A61N 5/10* (2006.01)
(Continued)

(52) U.S. Cl.
CPC ......... *A61N 5/1039* (2013.01); *A61N 5/1045* (2013.01); *A61N 5/1049* (2013.01);
(Continued)

(58) Field of Classification Search
CPC ................ H02H 7/001; G01V 3/00
(Continued)

(56) References Cited

U.S. PATENT DOCUMENTS 5,568,104 A * 10/1996 Laskaris ............ G01R 33/3806
324/318
5,939,962 A *  8/1999 Tahara ................. G01R 33/381
324/319
(Continued)

FOREIGN PATENT DOCUMENTS

JP        30217608 A    10/1985
JP      2001224571 A     8/2001
(Continued)

OTHER PUBLICATIONS

Raaymakers et al "Integrating a 1.5t MRI Scanner with a 6 MV Accelerator . . . " Phys. Med. Biol. 54 (2009) p. N229-N237.

*Primary Examiner* — Shawki S Ismail
*Assistant Examiner* — Lisa N Homza
(74) *Attorney, Agent, or Firm* — Sherry Austin

(57) ABSTRACT

A chamber (422) for a cryostat (420) includes: first and second annular sections (4221, 4222) separated and spaced apart from each other along a first direction, and a third annular section (4223) extending in the first direction between the first and second annular sections and connecting the first and second annular sections to each other. The first and second annular sections define corresponding first and second internal volumes, the third annular section defines a third internal volume, and the third internal volume is
(Continued)

substantially less than the first internal volume and substantially less than the second internal volume.

17 Claims, 5 Drawing Sheets

(51) Int. Cl.
*G01R 33/48* (2006.01)
*F17C 3/08* (2006.01)
*G01R 33/3815* (2006.01)
*H01F 6/04* (2006.01)
*H01F 6/06* (2006.01)

(52) U.S. Cl.
CPC ............ *A61N 5/1077* (2013.01); *F17C 3/085* (2013.01); *G01R 33/3815* (2013.01); *G01R 33/4808* (2013.01); *H01F 6/04* (2013.01); *H01F 6/06* (2013.01); *A61N 2005/1055* (2013.01)

(58) Field of Classification Search
USPC ......................................................... 335/216
See application file for complete search history.

(56) References Cited

U.S. PATENT DOCUMENTS

| | | | |
|---|---|---|---|
| 6,591,127 B1 * | 7/2003 | McKinnon ............... | A61B 6/00 378/63 |
| 7,057,391 B1 * | 6/2006 | Tanabe ............... | G01R 33/3806 324/318 |
| 7,960,710 B2 | 6/2011 | Kruip et al. | |
| 8,803,524 B2 | 8/2014 | Dempsey et al. | |
| 8,838,202 B2 | 9/2014 | Kruip | |
| 9,669,237 B2 * | 6/2017 | Calvert ................. | A61B 5/055 |
| 2006/0290351 A1 | 12/2006 | Matsumoto | |
| 2008/0208036 A1 * | 8/2008 | Amies ................. | A61N 5/1049 600/411 |
| 2011/0115485 A1 * | 5/2011 | Subbarao ............... | G01R 33/48 324/309 |
| 2011/0118588 A1 * | 5/2011 | Komblau ............ | A61N 5/1049 600/411 |
| 2011/0196226 A1 * | 8/2011 | Gross .................... | A61B 5/055 600/411 |
| 2011/0196227 A1 * | 8/2011 | Gross .................... | A61B 5/055 600/411 |
| 2011/0213239 A1 * | 9/2011 | Amies .................. | A61N 5/1049 600/411 |
| 2011/0304416 A1 | 12/2011 | Warner | |
| 2012/0184841 A1 * | 7/2012 | Nielsen ............... | A61N 5/1031 600/411 |
| 2013/0147476 A1 * | 6/2013 | Shvartsman ....... | G01R 33/3875 324/309 |
| 2013/0197351 A1 * | 8/2013 | Heid .................... | A61N 5/1049 600/411 |
| 2013/0218001 A1 * | 8/2013 | Uhlemann ............. | A61B 5/055 600/411 |
| 2013/0225974 A1 * | 8/2013 | Van Den Brink ... | A61N 5/1081 600/411 |
| 2013/0225975 A1 * | 8/2013 | Harvey ............... | A61B 5/0037 600/411 |
| 2013/0261430 A1 * | 10/2013 | Uhlemann ............ | A61N 5/1067 600/411 |
| 2014/0043027 A1 * | 2/2014 | Overweg ................ | A61B 5/055 324/319 |
| 2014/0084926 A1 * | 3/2014 | Amthor ............... | G01R 33/4808 324/309 |
| 2014/0135615 A1 * | 5/2014 | Kruip .................... | A61N 5/1049 600/411 |
| 2014/0221816 A1 * | 8/2014 | Franke ............... | G01R 33/4816 600/411 |
| 2014/0266206 A1 * | 9/2014 | Dempsey ......... | G01R 33/34092 324/322 |
| 2014/0275963 A1 * | 9/2014 | Shvartsman ........... | A61B 5/055 600/411 |
| 2014/0288349 A1 * | 9/2014 | Seeber ................ | A61N 5/1048 600/1 |
| 2015/0065860 A1 | 3/2015 | Shvartsman et al. | |
| 2015/0126799 A1 * | 5/2015 | Vahala ................. | A61N 5/1049 600/1 |
| 2015/0169836 A1 * | 6/2015 | Vahala .................... | A61N 7/02 600/411 |
| 2015/0224341 A1 * | 8/2015 | Vahala ............... | G01R 33/4808 600/411 |
| 2015/0323626 A1 * | 11/2015 | Jonas .................. | G01R 33/3804 324/322 |
| 2016/0011288 A1 * | 1/2016 | Overweg ........... | G01R 33/3875 600/411 |
| 2016/0023018 A1 * | 1/2016 | Zhang .................... | A61B 5/743 600/1 |
| 2016/0041240 A1 * | 2/2016 | Jonas ................. | G01R 33/3804 505/162 |
| 2016/0082288 A1 * | 3/2016 | Vahala ................. | A61N 5/1075 600/411 |
| 2016/0113570 A1 * | 4/2016 | Trausch ............... | A61N 5/1049 600/411 |
| 2016/0136456 A1 * | 5/2016 | Jonas ........................ | H01F 6/06 600/411 |
| 2016/0146911 A1 * | 5/2016 | Chmielewski ....... | A61N 5/1049 600/411 |
| 2016/0148375 A1 * | 5/2016 | Oh ........................ | G06T 11/008 382/131 |
| 2016/0189842 A1 * | 6/2016 | Jonas ........................ | H01F 6/04 335/216 |
| 2016/0213951 A1 * | 7/2016 | Uhlemann ........... | A61N 5/1049 |
| 2016/0256712 A1 * | 9/2016 | Vahala ................. | A61N 5/1038 |
| 2016/0263404 A1 * | 9/2016 | Mougenot ............ | A61N 5/1067 |
| 2016/0276082 A1 * | 9/2016 | Ackermann ....... | G01R 33/3804 |
| 2017/0014643 A1 * | 1/2017 | Wirtz ...................... | G01R 33/34 |
| 2017/0021195 A1 * | 1/2017 | Schweizer ........... | A61N 5/1039 |
| 2017/0065830 A1 * | 3/2017 | Vahala ................ | A61B 5/0555 |
| 2017/0080253 A1 * | 3/2017 | Clayton ................ | A61N 5/1067 |
| 2017/0097397 A1 * | 4/2017 | Jonas .................. | G01R 33/421 |
| 2017/0203123 A1 * | 7/2017 | Requardt ................. | G06T 7/97 |
| 2017/0263361 A1 * | 9/2017 | Mulder ..................... | H01F 6/04 |
| 2017/0363697 A1 * | 12/2017 | Jonas .................. | G01R 33/3804 |
| 2017/0368373 A1 * | 12/2017 | Sahadevan .......... | A61N 5/1084 |
| 2018/0078787 A1 * | 3/2018 | Schadewaldt ........ | A61N 5/1039 |
| 2018/0133518 A1 * | 5/2018 | Harper ................. | A61N 5/1045 |
| 2019/0079152 A1 * | 3/2019 | Raduma ................. | A61B 5/055 |

FOREIGN PATENT DOCUMENTS

| | | |
|---|---|---|
| RU | 2004114689 A | 10/2005 |
| WO | 20120143173 A1 | 10/2012 |

* cited by examiner

US 10,729,918 B2

CRYOSTAT AND SYSTEM FOR COMBINED MAGNETIC RESONANCE IMAGING AND RADIATION THERAPY

CROSS REFERENCE TO RELATED APPLICATIONS

This application is a U.S. national phase application of International Application No. PCT/IB2014/061962, filed on Jun. 5, 2014, which claims the benefit of U.S. provisional Application Ser. Nos. 61/837,739 filed on Jun. 21, 2013 and 61/882,924 filed Sep. 26, 2013 and are incorporated herein by reference.

TECHNICAL FIELD

The present invention generally pertains to a system capable of magnetic resonance imaging and radiation therapy, and a cryostat for such a system.

BACKGROUND AND SUMMARY

Magnetic resonance (MR) imagers or scanners have been developed that produce images for diagnosing disease and contrasting healthy tissue from abnormal tissue. An MR imager or scanner typically employs a superconducting magnet to generate the large magnetic fields which it requires for operation. To realize superconductivity, a magnet is maintained in a cryogenic environment at a temperature near absolute zero. Typically, the magnet includes one or more electrically conductive coils which are disposed in a cryostat and through which an electrical current circulates to create the magnetic field.

Meanwhile, radiation therapy has been developed which can focus a radiation beam (radiotherapy beam) on a target region of interest in a patient and preferentially destroy diseased tissue while avoiding healthy tissue.

It is desired to combine the diagnostic spatial specificity of MR imaging with radiotherapy beam focus technology to provide more accurate treatment of diseased tissue while reducing the damage of healthy tissue. By combining real time imaging and radiation therapy, radiotherapy beam shaping may be performed in real time, compensating for not only daily changes in anatomy but also body movements such as breathing which occur during the treatment procedure.

In operation, a radiotherapy beam may be rotated around a patient to deposit a focused dose of radiation at the target area (i.e., diseased tissue) while sparing the healthy tissue. Combining radiation therapy with MR imaging requires that the radiotherapy beam reach a patient who is enclosed with an MR imager and scanner. Furthermore, the radiation beam should pass through the MR imager or scanner in a controlled and known manner so that the magnitude and location of energy delivered by the radiotherapy beam can be accurately controlled.

In general, the most accurate MR imagers or scanners use high magnetic fields produced by superconducting magnets which usually are composed of thick superconducting wire windings, thin metallic shells and a large cryogenic bath (e.g., liquid helium) disposed in a cryostat.

A radiotherapy beam is attenuated when it passes through matter such as metals or even liquid helium in a cryostat of the MR imager or scanner. If the attenuation or loss is held constant over time and angular position, it is possible to compensate or adjust for the loss so as to accurately control the magnitude and location of energy delivered by the radiotherapy beam.

However, during maintenance and operation of the superconducting magnet system of an MR imager or scanner, it is often the case that some amount of cryogenic fluid (e.g., liquid helium) boils off and therefore the level changes, thereby changing the attenuation of the radiotherapy beam. Furthermore, since the cryostat is typically not completely filled with liquid helium, the amount of liquid helium varies as a function of position within the cryostat, and the amount or volume of liquid helium through which the radiotherapy beam must pass may also be a function of angular position. As a result, attenuation of the radiotherapy beam is also a function of angular position. Thus it may be difficult to accurately control the amount of radiation energy delivered to a target area of interest by the radiotherapy beam to be constant, and particularly to be constant at various angular positions.

One aspect of the present invention can provide an apparatus, comprising a radiation source configured to generate a radiotherapy beam and a magnetic resonance imager. The magnetic resonance imager can include a cryostat. The cryostat can comprise: an inner chamber, and a vacuum region substantially enclosing the inner chamber. The inner chamber can comprise: first and second annular sections separated and spaced apart from each other along a first direction, and a third annular section extending in the first direction between the first and second annular sections and connecting the first and second annular sections to each other. An internal width of the third annular section in a plane perpendicular to the first direction can be less than an internal width of the first annular section and an internal width of the second annular section. The radiotherapy beam can be configured to pass through the third annular section of the cryostat In some embodiments, the radiation source can comprise a linear accelerator.

In some embodiments, the radiation source can comprise a multileaf collimator.

In some embodiments, the apparatus can further include superconducting coils disposed in the first and second annular sections. The superconducting coils can include at least a pair of first semiconductor coils and a pair of second semiconductor coils, wherein the first superconducting coils can be disposed closer than the second superconducting coils to the third annular section, and wherein a diameter of each of the first superconducting coils can be greater than a diameter of each of the second superconducting coils.

In some embodiments, the radiotherapy beam can be configured to pass between the pair of first semiconductor coils.

In some embodiments, the first and second annular sections can have disposed therein corresponding first and second annular volumes of a cryogenic fluid, the third annular section can have disposed therein a third annular volume of the cryogenic fluid, and an annular depth of the third annular volume in the plane perpendicular to the first direction can be less than an annular depth of the first annular volume and an annular depth of the second annular volume.

In some embodiments, the apparatus can include a tubular structure extending in the first direction between the first and second annular sections.

Another aspect of the invention can provide a chamber for a cryostat. The chamber can include first and second annular sections separated and spaced apart from each other along a first direction, and a third annular section extending in the first direction between the first and second annular sections and connecting the first and second annular sections to each other. The first and second annular sections can define corresponding first and second internal volumes, the third annular section can define a third internal volume, and the third internal volume can be substantially less than the first internal volume and substantially less than the second internal volume.

In some embodiments, the first and second annular sections can have disposed therein corresponding first and second annular volumes of a cryogenic fluid, the third annular section can have disposed therein a third annular volume of the cryogenic fluid, and an average annular depth of the third volume in the plane perpendicular to the first direction can be less than an average annular depth of the first volume and an average annular depth of the second volume.

In some embodiments, the cryogenic fluid can comprise liquid helium.

In some embodiments, the cryogenic fluid can comprise gaseous helium.

In some embodiments, the first internal volume and the second internal volume each can be ten times the third internal volume.

In some embodiments, the first internal volume and the second internal volume each can be one hundred times the third internal volume.

In some embodiments, the chamber can include superconducting coils disposed in the first and second annular sections. The superconducting coils can include at least a first semiconductor coil and a second semiconductor coil, wherein the first superconducting coil can be disposed closer than the second superconducting coil to the third annular section, and wherein a diameter of the first superconducting coil can be greater than a diameter of the second superconducting coil.

In some embodiments, the internal width of the first annular section and the internal width of the second annular section each can be more than ten times the internal width of the third annular section.

In some embodiments, the internal width of the first annular section and the internal width of the second annular section each can be more than thirty times the internal width of the third annular section.

Yet another aspect of the invention can provide a chamber for a cryostat. The chamber can comprise first and second annular sections separated and spaced apart from each other along a first direction, and a third annular section extending in the first direction between the first and second annular sections and connecting the first and second sections to each other. The first and second annular sections can have disposed therein corresponding first and second annular volumes of a cryogenic fluid. The third annular section can have a third annular volume of the cryogenic fluid disposed therein. The an average annular depth of the third annular volume in a plane perpendicular to the first direction can be less than the average annular depth of the first annular volume and the average annular depth of the second annular volume.

In some embodiments, the chamber can include superconducting coils disposed in the first and second annular sections. The superconducting coils can include at least a first semiconductor coil and a second semiconductor coil, wherein the first superconducting coil is disposed closer than the second superconducting coil to the third annular section, and wherein a diameter of the first superconducting coil is greater than a diameter of the second superconducting coil.

In some embodiments, an internal width of the first annular section in the plane perpendicular to the first direction and an internal width of the second annular section in the plane perpendicular to the first direction each can be more than ten times an internal width of the third annular section in the plane perpendicular to the first direction.

In some embodiments, an internal width of the first annular section in the plane perpendicular to the first direction and an internal width of the second annular section in the plane perpendicular to the first direction each can be more than thirty times an internal width of the third annular section in the plane perpendicular to the first direction.

BRIEF DESCRIPTION OF THE DRAWINGS

The present invention will be more readily understood from the detailed description of exemplary embodiments presented below considered in conjunction with the accompanying drawings.

DETAILED DESCRIPTION

The present invention will now be described more fully hereinafter with reference to the accompanying drawings, in which embodiments of the present invention are shown. The present invention may, however, be embodied in different forms and should not be construed as limited to the embodiments set forth herein. Rather, these embodiments are provided as teaching examples of the invention. Within the present disclosure and claims, when something is said to have approximately a certain value, then it means that it is within 10% of that value, and when something is said to have about a certain value, then it means that it is within 25% of that value. When something is said to be substantially greater, then it means that it is at least 10% greater, and when something is said to be substantially less, then it means that it is at least 10% less.

Figure 1:
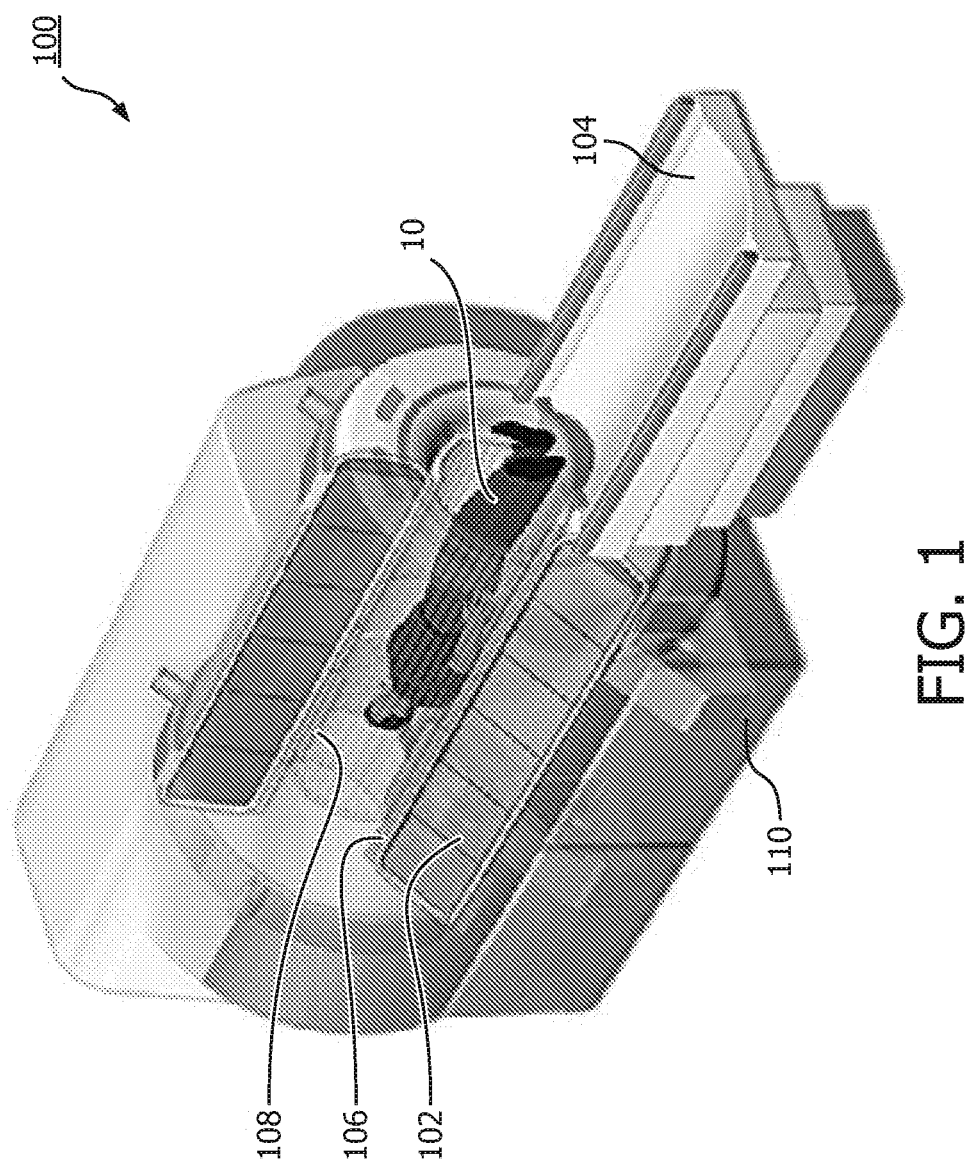
FIG. 1 illustrates an exemplary embodiment of a magnetic resonance (MR) imager.

FIG. 1 illustrates an exemplary embodiment of a magnetic resonance (MR) imager 100. MR imager 100 may include a magnet 102; a patient table 104 configured to hold a patient 10; gradient coils 106 configured to at least partially surround at least a portion of patient 10 for which MR imager 100 generates an image; a radio frequency coil 108 configured to apply a radio frequency signal to at least the portion of patient 10 which is being imaged, and to alter the alignment of the magnetic field; and a scanner 110 configured to detect changes in the magnetic field caused by the radio frequency signal.

The general operation of an MR imager is well known and therefore will not be repeated here.

Figure 2:
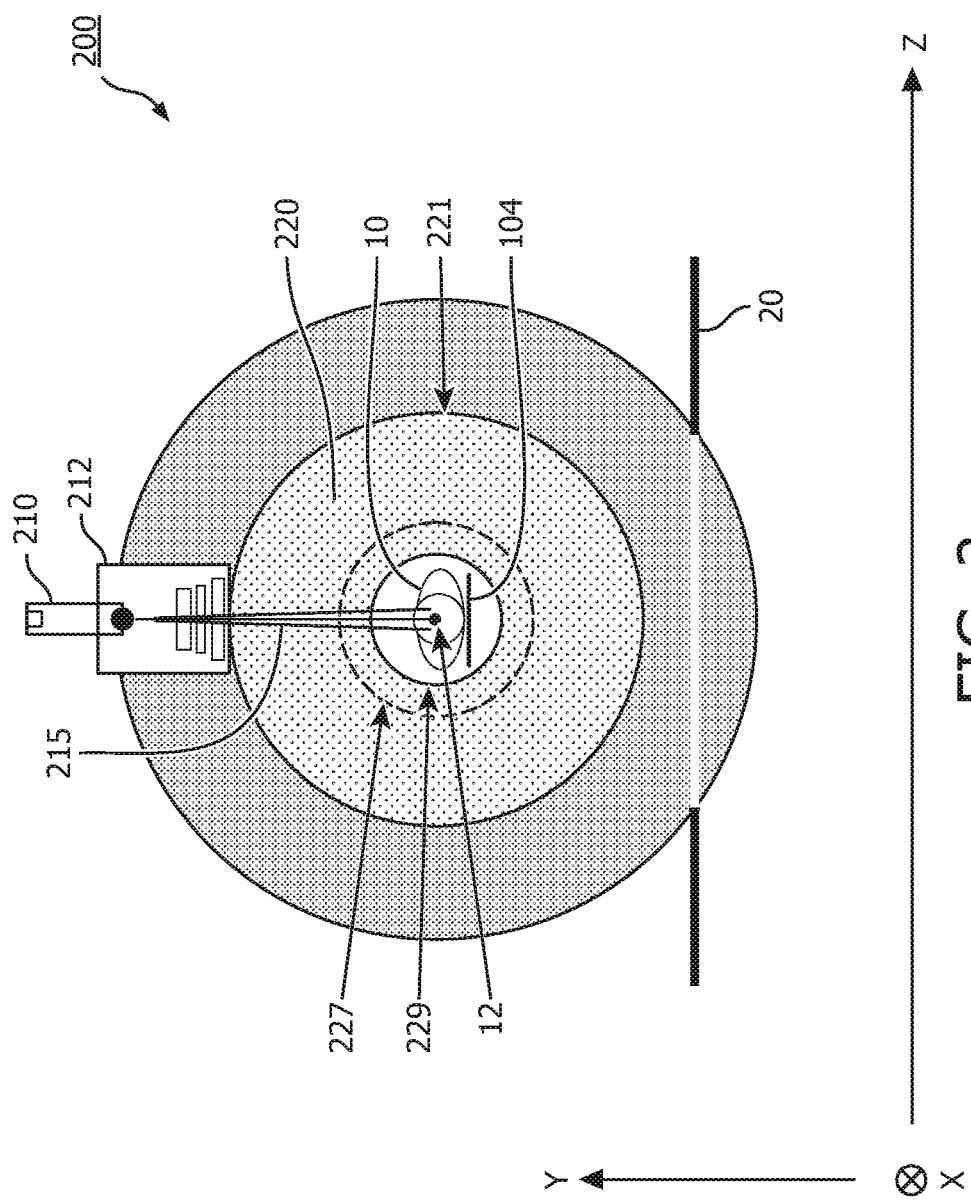
FIG. 2 illustrates a cross-sectional view of a combined magnetic resonance imager and radiotherapy apparatus.

FIG. 2 illustrates a cross-sectional view of a combined magnetic resonance (MR) imager and radiotherapy apparatus 200. Apparatus 200 includes a radiation source comprising a gun section 210 and a linear accelerator 212 for producing a radiotherapy beam 215. In some embodiments, the radiation source may further include a multileaf collimator. Apparatus 200 further includes an MR imager including a cryostat 220 having a superconducting magnet (not shown) and a cryogenic fluid disposed therein for cooling the superconducting magnet. For simplicity of illustration, some components of the MR imager, such as gradient coils, an RF coil, etc. are omitted from FIG. 2. Cryostat 220 has an outer wall 221, an inner bore 227. The MR imager has an inner bore 229 inside of which is disposed patient table 104 which is configured to hold a patient 10. Apparatus 200 may be mounted in or on a floor 20.

In operation, the MR imager may produce MR images of patient 10, or at least a region of interest 12 in patient 10. For example, region of interest 12 may comprise diseased tissue to be treated with radiotherapy beam 215. Meanwhile, radiotherapy beam 215 may be rotated around patient 10 in the Y-Z plane as denoted in FIG. 2 to provide a focused dose of radiation to region of interest 12. Apparatus 200 may combine the diagnostic spatial specificity of MR imaging with radiation therapy beam focus technology to provide more accurate treatment of diseased tissue while reducing damage to healthy tissue. By combining real time imaging and radiation therapy, beam shaping may be performed real time compensating for not only daily changes in anatomy but also body movements such as breathing, to produce a more accurate delivery of the radiotherapy beam.

Figure 3:
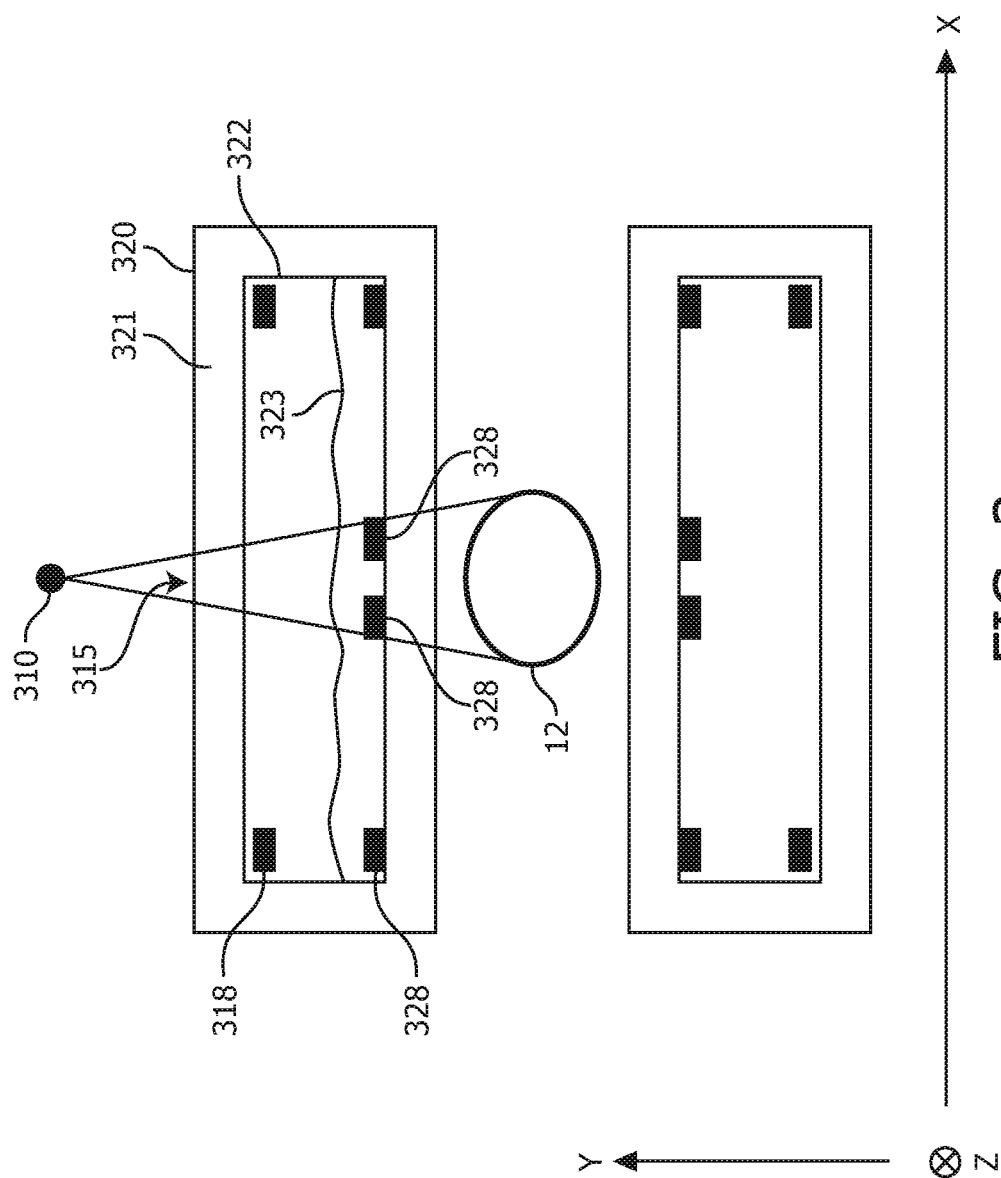
FIG. 3 conceptually illustrates one or more problems which may occur when combining a magnetic resonance imager and a radiotherapy apparatus.

FIG. 3 conceptually illustrates one or more problems which may occur when combining a magnetic resonance (MR) imager and a radiotherapy apparatus. FIG. 3 illustrates a radiation source 310, generating a radiotherapy beam 315, and a cryostat 320 of the MR imager, through which radiotherapy beam 315 must pass to reach a region of interest 12, for example diseased tissue of a patient to be treated with radiotherapy beam 315. For simplicity of illustration, some components of the MR imager, such as gradient coils, an RF coil, etc. are omitted from FIG. 3.

Cryostat 320 includes an inner chamber 322 which is surrounded or substantially (i.e., at least 90%) surrounded by a vacuum region 321. Disposed within inner chamber 322 are a superconducting magnet comprising superconducting coils 328 and a cryogenic fluid 323. In some embodiments, cryogenic fluid 323 may comprise liquid helium. In some embodiments, a cryogenic fluid of helium gas also may be disposed within inner chamber 322 of cryostat 320. Also disposed within inner chamber 322 are shield coils 318. In some embodiments, shield coils 318 may not be disposed within cryostat 320.

In operation, the MR imager may produce MR images of a patient, or at least region of interest 12, in the patient. For example, region of interest 12 may comprise diseased tissue to be treated with radiotherapy beam 315. Meanwhile, radiation source 310 may rotate in the Y-Z plane as denoted in FIG. 3 around region of interest 12 so as to cause radiotherapy beam 315 to also be rotated around region of interest 12 to provide a focused dose of radiation to region of interest 12.

As illustrated in FIG. 3, radiotherapy beam 315 must pass through a portion of cryogenic fluid 323 to reach region of interest 12. Radiotherapy beam 315 is attenuated when it passes through cryogenic fluid 323 (e.g., liquid helium), and the amount of attenuation is a function of the volume or depth of cryogenic fluid 323 though which radiotherapy beam 315 passes.

As explained above, radiotherapy beam 315 should pass through the MR imager or scanner in a controlled and known manner so that the magnitude and location of energy delivered by radiotherapy beam 315 can be accurately controlled. Furthermore, the attenuation factor of the radiotherapy beam should be constant at various angular positions and should be kept to a minimum.

However, during maintenance and operation of the superconducting magnet system it is usual that some amount of cryogenic fluid 323 (e.g., liquid helium) boils off and therefore the volume or depth changes, thereby changing the attenuation of radiotherapy beam 315. Furthermore, with inner chamber 322 of cryostat 320 not being completely filled with cryogenic fluid 323 (e.g., liquid helium), the amount of cryogenic fluid 323 (e.g., liquid helium) through which radiotherapy beam 315 must pass may also be a function of angular position in the Y-Z plane, so that the attenuation of radiotherapy beam 315 is also a function of angular position in the Y-Z plane. Thus it may be difficult to accurately control radiotherapy beam 315 to have a constant level, and particularly to be constant at various angular positions.

Additionally, as illustrated in FIG. 3, some of the superconducting coils 328 are disposed in the path of radiotherapy beam 315 to reach region of interest 12. Furthermore these superconducting coils 328 cannot simply be removed without destroying the uniformity of the magnetic field which is important for generating accurate MR images.

Figure 4:
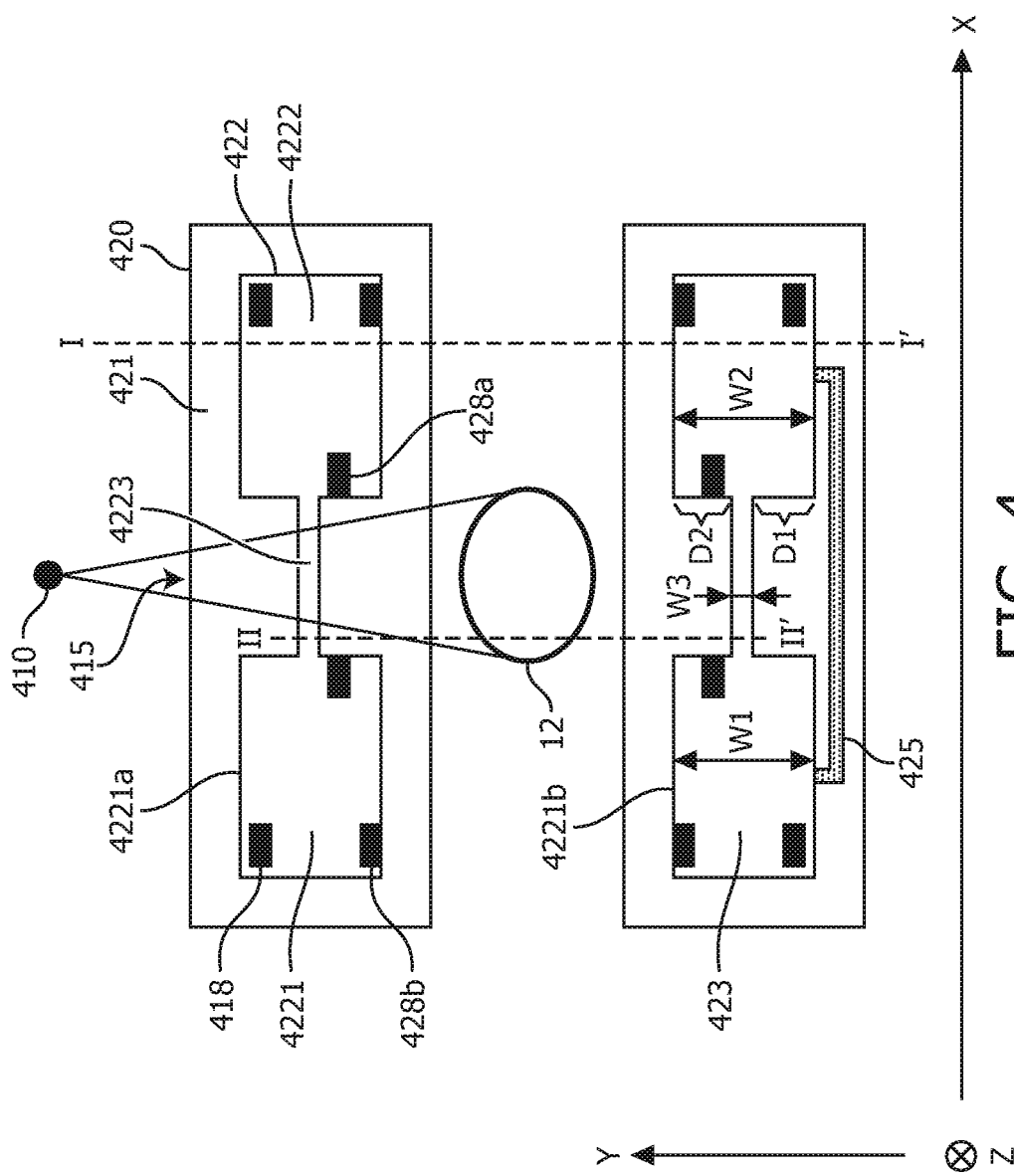
FIG. 4 illustrates a cross-sectional view of an embodiment of an apparatus for combined magnetic resonance imaging and radiotherapy which may overcome one or more problems illustrated in FIG. 3.

FIG. 4 illustrates a cross-sectional view of an embodiment of an apparatus 400 for combined magnetic resonance imaging and radiotherapy which may overcome one or more problems illustrated in FIG. 3. Apparatus 400 includes a radiation source 410 and an MR imager which further includes a cryostat 420. For simplicity of illustration, some components of the MR imager, such as gradient coils, an RF coil, etc. are omitted from FIG. 4.

Radiation source 410 may include a linear accelerator and a multileaf collimator which may generate a radiotherapy beam 415 as illustrated in FIG. 4.

Cryostat 420 includes an inner chamber 422 which is surrounded or substantially (i.e., at least 90%) surrounded by a vacuum region 421. Inner chamber 422 comprises a first annular section 4221 and a second annular section 4222 separated and spaced apart from each other along the X direction ("a first direction"), and a third or center annular section 4223 extending in the X direction between first and second annular sections 4221, 4222 and connecting first and second annular sections 4221, 4222 to each other.

Inner chamber 422 is configured to hold therein a volume of a cryogenic fluid 423 when apparatus 400 is in operation. In some embodiments, cryogenic fluid 423 may comprise liquid helium. In some embodiments, a cryogenic fluid of helium gas also may be disposed within inner chamber 422 of cryostat 420.

Beneficially, third annular section 4223 may be configured to hold therein a substantially smaller volume of cryogenic fluid 423 than each of first and second annular sections 4221, 4222 are configured to hold therein. In some embodiments, one or both of first and second annular sections 4221, 4222 may hold therein a volume of cryogenic fluid 423 which is at least 100 times greater than a volume of cryogenic fluid 423 which third annular section 4223 holds therein. In some embodiments, one or both of first and second annular sections 4221, 4222 may hold therein a volume of cryogenic fluid 423 which is more than 1000 times greater than a volume of cryogenic fluid 423 which third annular section 4223 holds therein.

In particular, in some embodiments the average annular depth of cryogenic fluid 423 in third annular section 4223 in the Y-Z plane (i.e., a plane perpendicular to the X direction) may be substantially less than the average annular depth of cryogenic fluid 423 in one or both of first and second annular sections 4221, 4222. In some embodiments the average annular depth of cryogenic fluid 423 in third annular section 4223 may less than about 10% of the average annular depth of cryogenic fluid 423 in one or both of first and second annular sections 4221, 4222. In some embodiments the average annular depth of cryogenic fluid 423 in third annular section 4223 may about 3% of the average annular depth of cryogenic fluid 423 in one or both of first and second annular sections 4221, 4222.

Toward this end, as shown in FIG. 4 first annular section 4221 defines a first internal volume, second annular section 4222 defines a second internal volume, and third annular section 4223 defines a third internal volume. In some embodiments, one or both of the first internal volume defined by first annular section 4221 and the second internal volume defined by second annular section 4222 may be at least 100 times greater than the third internal volume defined by third annular section 4223. In some embodiments, one or both of the first internal volume defined by first annular section 4221 and the second internal volume defined by second annular section 4222 may be at least 1000 times greater than the third internal volume defined by third annular section 4223.

To achieve this, the relative sizes of the internal dimensions of inner chamber 422 in first, second and third annular sections 4221, 4222 and 4223 may be proportioned as shown, for example, in FIG. 4. In particular, in an embodiment as illustrated in FIG. 4, the internal width W3 of third annular section 4223 in the Y-Z plane perpendicular to the X direction is less than the internal width W1 of first annular section 4221 and the internal width W2 of second annular section 4222 in the Y-Z plane. Here, an internal width is understood to mean a cross-sectional dimension of the interior of inner chamber 422, and thus excludes the thickness of the wall of inner chamber 422.

Figure 5B:
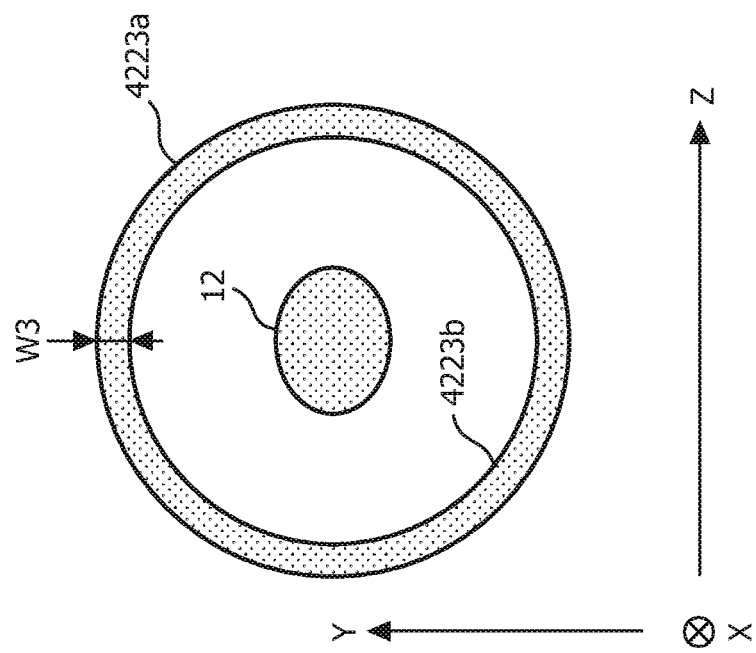
FIGS. 5A and 5B illustrate other cross-sectional views of an embodiment of an apparatus for combined magnetic resonance imaging and radiotherapy.
Figure 5A:
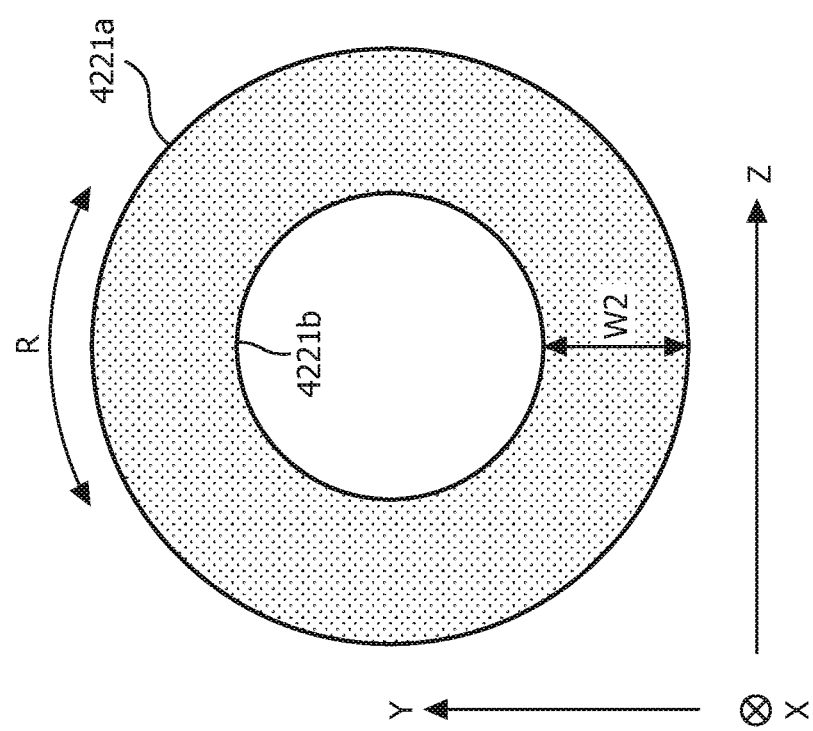

FIG. 5A illustrates a cross-sectional view along line I-I' in FIG. 4 showing an example of a cross-section in the Y-Z plane of second annular section 4222, and FIG. 5B illustrates a cross-sectional view along line II-II' in FIG. 4 showing an example of a cross-section in the Y-Z plane of third annular section 4223 for one embodiment of apparatus 400. In some embodiments, the cross-section in the Y-Z plane of first annular section 4221 may be the same as the cross-section in the Y-Z plane of second annular section 4222, and for simplicity of explanation, it will be assumed in the discussion to follow that this is the case. However, it should be understood that in general, this is not required.

As shown in FIG. 4 and FIG. 5A, first and second annular sections 4221, 4222 are defined in part by a substantially circular outer surface 4221a and a substantially circular inner surface 4221b. Although FIGS. 4 and 5A illustrate an embodiment where inner and outer surfaces 4221a and 4221b are substantially circular, in other embodiments they may take up other shapes, for example ovular or rectangular, and they may have different shapes than each other. As shown in FIG. 5B, third annular section 4223 is defined in part by a substantially circular outer surface 4223a and a substantially circular inner surface 4223b. Although FIG. 5B illustrates an embodiment where inner and outer surfaces 4222a and 4223b are substantially circular, in other embodiments they may take up other shapes, for example ovular or rectangular, and they may have different shapes than each other.

That is, first and second annular sections 4221, 4222 and 4223 may take the shape of a circular ring, an ovular ring, a rectangular ring, or some other ring shape.

Although the embodiment of FIGS. 4 and 5A-B illustrates third annular section 4223 as a single passageway connecting first and second annular sections 4221, 4222 to each other, other embodiments are contemplated which include multiple passageways connecting first and second annular sections 4221, 4222 to each other, so long as the level of cryogenic fluid through which radiotherapy beam 415 passes is maintained.

As illustrated in FIG. 4, inner chamber 422 of cryostat may be viewed as having a first notch of depth D1 in the outer surface thereof at center annular section 4223, and further having a second notch of depth D2 in the inner surface thereof at center annular section 4223. Although as illustrated in FIGS. 4, 5A and 5B, the depths D1 and D2 are equal to each other, in some embodiments the depths D1 and D2 may be different than each other. In some embodiments, the depth D1 or the depth D2 may be zero or substantially zero.

Beneficially, the internal width W3 of third or central annular section 4223 may be made as thin as possible, while still providing structural integrity and allowing for thermal communication between first and second annular sections 4221, 4222 of inner chamber 422, for example by an exchange of cryogenic fluid 423 between first and second annular sections 4221, 4222 which may maintain a thermal equilibrium. In some embodiments, the internal width W3 is greater than 5 mm.

In some embodiments, one or both of the internal width W1 of first annular section 4221 and the internal width W2 of second annular section 4222 may be more than ten times the internal width of third annular section 4223. For example, in some embodiments the internal widths W1 and W2 may each be 500 mm, and the internal width W3 may be less than 50 mm.

In some embodiments, one or both of the internal width W1 of first annular section 4221 and the internal width W2 of second annular section 4222 may be more than thirty times the internal width of third annular section 4223. For example, in some embodiments the internal widths W1 and W2 may each be about 500 mm, or approximately 500 mm, and the internal width W3 may be about 15 mm, or approximately 15 mm.

First and second annular sections 4221, 4222 have disposed therein a plurality of superconducting coils, including first or central superconducting coil(s) 428a and second superconducting coil(s) 428b. In some embodiments, no superconducting coil(s) are disposed within third or central annular section 4223. Also disposed within first and second annular sections 4221, 4222 of inner chamber 422 are shield coils 418. In some embodiments, shield coils 418 may not be disposed within cryostat 420.

In a beneficial arrangement, as illustrated in FIG. 4 first or central superconducting coil(s) 428a may be disposed closer than second superconducting coil(s) 428b to third annular section 4223, and the diameter of first or central superconducting coil(s) 428a may be greater than the diameter of the second superconducting coil(s) 428b which are located at opposite ends of first and second annular sections 4221, 4222. Because first or central superconducting coil(s) 428a should be outside of the path of radiotherapy beam 415, in apparatus 400 they are split farther apart in comparison to the arrangement illustrated in FIG. 3, to permit radiotherapy beam 415 to pass therebetween. However, by increasing the radius/diameter of first or central superconducting coil(s) 428a, for example with respect to second superconducting coil(s) 428b which are located at opposite ends of first and second annular sections 4221, 4222, it becomes possible to maintain a uniform magnetic field for proper MR imaging.

Also illustrated in FIG. 4 is a tubular structure 425 extending in the X direction between first and second annular sections 4221 and 4222. Tubular structure 425 may pass a gas (e.g., helium gas) and/or one or more electrical wires and/or other structural components between first and second annular sections 4221 and 4222. In some embodiments, tubular structure 425 may have a width or cross-section of about 5 mm.

In operation, the MR imager may produce MR images of a patient, or at least region of interest 12, in the patient. For example, region of interest 12 may comprise diseased tissue to be treated with radiotherapy beam 415. Meanwhile, radiation source 410 may rotate in the Y-Z plane as denoted in FIG. 4 (the "R" direction as shown in FIG. 5A) around region of interest 12 so as to cause radiotherapy beam 415 to also be rotated around region of interest 12 to provide a focused dose of radiation to region of interest 12.

As illustrated in FIG. 4, radiotherapy beam 415 passes through third or central annular region 4223 of inner chamber 422 of cryostat 420 to reach region of interest 12. Accordingly, radiotherapy beam 415 passes through the relatively thin volume or annular depth of cryogenic fluid 423 (e.g., liquid helium) in third or central annular region 4223, while a relatively large volume or annular depth of cryogenic fluid 423 (e.g., liquid helium) remains in the interconnected first and second annular regions 4221 and 4222 containing and cooling superconducting coils 428a, 428b. Beneficially, third or central annular region 4223 of inner chamber 422 has a sufficiently thin annular volume of cryogenic fluid 423 (e.g., liquid helium) in the path of radiotherapy beam 415 such that a change in the level cryogenic fluid 423 (e.g., liquid helium) does not significantly affect the dose of radiation applied to region of interest 12 of a patient 10. Meanwhile, the relatively large volume of cryogenic fluid 423 (e.g., liquid helium) in first and second annular regions 4221 and 4222 through which radiotherapy beam 415 does not pass provides a thermal reservoir for maintenance and operation of cryostat 420. Beneficially, third or central annular region 4223 (i.e., a internal width W3 of third or central annular region 4223) is sized to allow thermal communication between first and second annular regions 4221 and 4222, allow for manufacturing tolerances, and still reduce both absorption of radiotherapy beam 415 and angular variation as radiotherapy beam 415 is rotated in the Y-Z plane. Additionally, providing a vacuum recess in vacuum region 421 from both inner wall 4221b and outer wall 4221a (i.e., depths D1 and D2 shown in FIG. 4) may naturally create a mechanical structure which enables first or central superconducting coils 428a to have a larger diameter/radius than superconducting coils 428b located at the opposite ends of first and second annular regions 4221 and 4222. By providing thermal communication between first and second annular regions 4221 and 4222 of inner chamber 422 by means of the connected third or central annular region 4223, the design and construction of cryostat 420 may be simplified when compared, for example, to a cryostat which included two separate and thermally isolated inner chambers.

While preferred embodiments are disclosed herein, many variations are possible which remain within the concept and scope of the invention. Such variations would become clear to one of ordinary skill in the art after inspection of the specification, drawings and claims herein. The present invention therefore is not to be restricted except within the scope of the appended claims.

What is claimed is:

1. An apparatus, comprising:
a radiation source configured to generate a radiotherapy beam; and
a magnetic resonance imager,
wherein the magnetic resonance imager includes a cryostat, the cryostat comprising:
an inner chamber, and
a vacuum region substantially enclosing the inner chamber,
wherein the inner chamber comprises:
first and second annular sections separated and spaced apart from each other along a first direction, and
a third annular section extending in the first direction between the first and second annular sections and connecting the first and second annular sections to each other,
wherein an internal width of the third annular section in a plane perpendicular to the first direction is less than an internal width of the first annular section and an internal width of the second annular section,
wherein the radiotherapy beam is configured to pass through the third annular section of the cryostat,
wherein the apparatus further comprises superconducting coils disposed in the first and second annular sections, the superconducting coils including at least a pair of first superconducting coils and a pair of second superconducting coils, wherein the first superconducting coils are disposed closer than the second superconducting coils to the third annular section, and wherein a diameter of each of the first superconducting coils is greater than a diameter of each of the second superconducting coils.

2. The apparatus of claim 1, wherein the radiation source comprises at least one of a linear accelerator or a multileaf collimator.

3. The apparatus of claim 1, wherein the first and second annular sections have disposed therein corresponding first and second annular volumes of a cryogenic fluid, wherein the third annular section has disposed therein a third annular volume of the cryogenic fluid, and wherein an annular depth of the third annular volume in the plane perpendicular to the first direction is less than an annular depth of the first annular volume and an annular depth of the second annular volume.

4. The apparatus of claim 1, further comprising a tubular structure extending in the first direction between the first and second annular sections and connecting the first and second annular sections to each other.

5. The apparatus of claim 1, wherein an outer diameter of the cryostat is substantially constant.

6. A chamber for a cryostat, comprising:
first and second annular sections separated and spaced apart from each other along a first direction, the first and second annular sections having disposed therein corresponding first and second annular volumes of a cryogenic fluid;

a third annular section extending in the first direction between the first and second annular sections and connecting the first and second annular sections to each other, the third annular section having a third annular volume of the cryogenic fluid disposed therein; and a tubular structure separate and apart from the third annular section extending in the first direction between the first and second annular sections and connecting the first and second annular sections to each other, wherein an average annular depth of the third annular volume in a plane perpendicular to the first direction is less than an average annular depth of the first annular volume and an average annular depth of the second annular volume.

7. The chamber of claim 6, further comprising superconducting coils disposed in the first and second annular sections, the superconducting coils including at least a first superconducting coil and a second superconducting coil, wherein the first superconducting coil is disposed closer than the second superconducting coil to the third annular section, and wherein a diameter of the first superconducting coil is greater than a diameter of the second superconducting coil.

8. The chamber of claim 6, wherein an internal width of the first annular section in the plane perpendicular to the first direction and an internal width of the second annular section in the plane perpendicular to the first direction are each more than ten times an internal width of the third annular section in the plane perpendicular to the first direction.

9. The chamber of claim 6, wherein an internal width of the first annular section in the plane perpendicular to the first direction and an internal width of the second annular section in the plane perpendicular to the first direction are each more than thirty times an internal width of the third annular section in the plane perpendicular to the first direction.

10. The chamber of claim 6, wherein an internal width of the third annular section in the plane perpendicular to the first direction is less than an internal width of the first annular section and an internal width of the second annular section.

11. The chamber of claim 6, wherein the first and second annular sections define corresponding first and second internal volumes, wherein the third annular section defines a third internal volume, and wherein the third internal volume is substantially less than the first internal volume and substantially less than the second internal volume.

12. The chamber of claim 6, wherein the first and second annular sections define corresponding first and second internal volumes, wherein the third annular section defines a third internal volume, wherein the first internal volume and the second internal volume are each at least one hundred times the third internal volume.

13. An apparatus, comprising:
a radiation source configured to generate a radiotherapy beam; and
a magnetic resonance imager,
wherein the magnetic resonance imager includes a cryostat, the cryostat comprising:
an inner chamber, and
a vacuum region substantially enclosing the inner chamber,
wherein the inner chamber comprises:
first and second annular sections separated and spaced apart from each other along a first direction, and
a third annular section extending in the first direction between the first and second annular sections and connecting the first and second annular sections to each other,
wherein an internal width of the third annular section in a plane perpendicular to the first direction is less than an internal width of the first annular section and an internal width of the second annular section,
wherein the radiotherapy beam is configured to pass through the third annular section of the cryostat,
wherein the radiotherapy beam is configured to pass between the pair of first superconducting coils.

14. The apparatus of claim 13, wherein the radiation source comprises at least one of a linear accelerator or a multileaf collimator.

15. The apparatus of claim 13, wherein the first and second annular sections have disposed therein corresponding first and second annular volumes of a cryogenic fluid, wherein the third annular section has disposed therein a third annular volume of the cryogenic fluid, and wherein an annular depth of the third annular volume in the plane perpendicular to the first direction is less than an annular depth of the first annular volume and an annular depth of the second annular volume.

16. The apparatus of claim 13, further comprising a tubular structure extending in the first direction between the first and second annular sections and connecting the first and second annular sections to each other.

17. The apparatus of claim 13, wherein an outer diameter of the cryostat is substantially constant.

\* \* \* \* \*